(12) United States Patent
Kitaoka

(10) Patent No.: US 6,170,267 B1
(45) Date of Patent: Jan. 9, 2001

(54) SAMPLE COOLING APPARATUS AND METHODS

(75) Inventor: Mitsuo Kitaoka, Kyoto (JP)

(73) Assignee: Shimadzu Corporation, Kyoto (JP)

(*) Notice: Under 35 U.S.C. 154(b), the term of this patent shall be extended for 0 days.

(21) Appl. No.: 09/354,554

(22) Filed: Jul. 15, 1999

(30) Foreign Application Priority Data

Aug. 28, 1998 (JP) ................................................. 10-243918

(51) Int. Cl.⁷ ................................................. F25B 21/02
(52) U.S. Cl. ............................................ 62/3.6; 62/457.9
(58) Field of Search ............................... 62/3.4, 3.6, 3.7, 62/457.9

(56) References Cited

U.S. PATENT DOCUMENTS

| | | | |
|---|---|---|---|
| 5,029,446 | * 7/1991 | Sukuki | 62/3.6 |
| 5,320,162 | * 6/1994 | Seaman | 165/2 |
| 5,504,007 | * 4/1996 | Haynes | 435/285.1 |
| 5,635,397 | * 6/1997 | Futschik et al. | 435/286.1 |
| 5,881,560 | * 3/1999 | Bielinski | 62/3.2 |
| 6,038,865 | * 3/2000 | Watanabe et al. | 62/3.6 |

FOREIGN PATENT DOCUMENTS

| | | | |
|---|---|---|---|
| 2111301 | * 6/1983 | (GB) | 62/3.6 |
| 6-117661 | * 4/1994 | (JP) | 62/3.4 |

* cited by examiner

Primary Examiner—William Doerrler
Assistant Examiner—Melvin Jones
(74) Attorney, Agent, or Firm—Majestic, Parsons, Siebert & Hsue P.C.

(57) ABSTRACT

A sample cooler has a thermostatic chamber containing a heat-conducting block on which vessels containing liquid samples are set. A control unit activates a cooling mechanism of the air cooling type to cool the air inside the thermostatic chamber. Thereafter, when the temperature or humidity inside the thermostatic chamber is detected to have reached a specified level, when condensation of dew is detected inside the thermostatic chamber, or when a predetermined time has elapsed, the control unit starts to operate another cooling mechanism of the direct cooling type to cool the heat-conducting block, such that the samples can be cooled directly and quickly under a dehumidified condition without causing dew condensation.

16 Claims, 2 Drawing Sheets

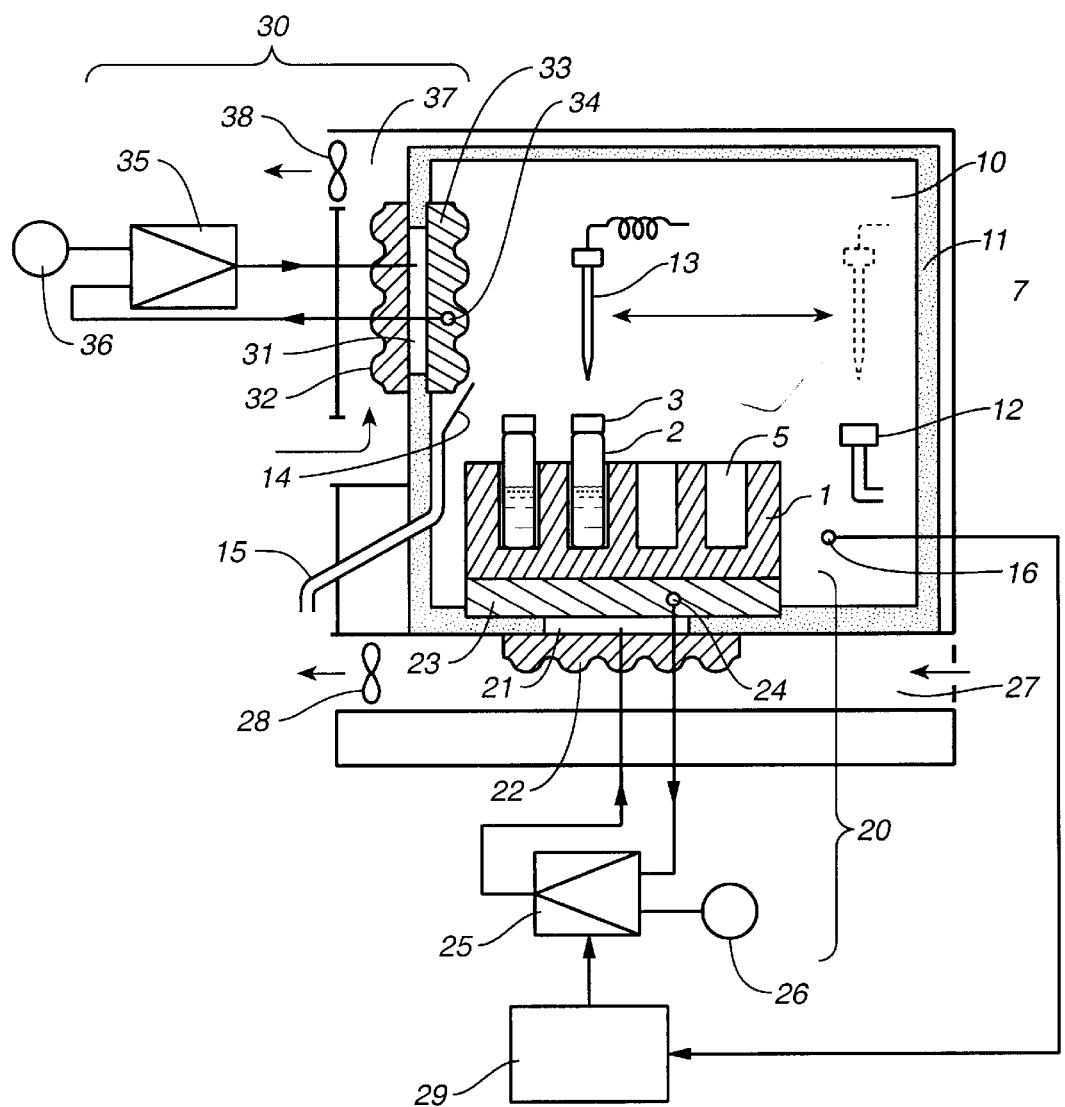
FIG._1

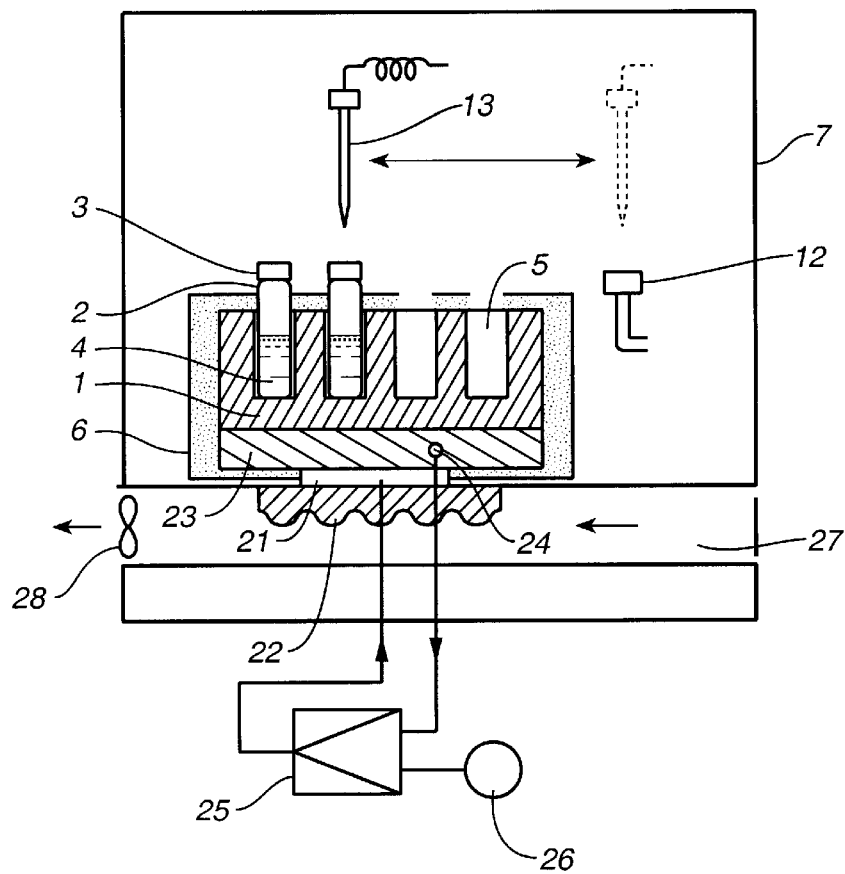
FIG._2
(PRIOR ART)
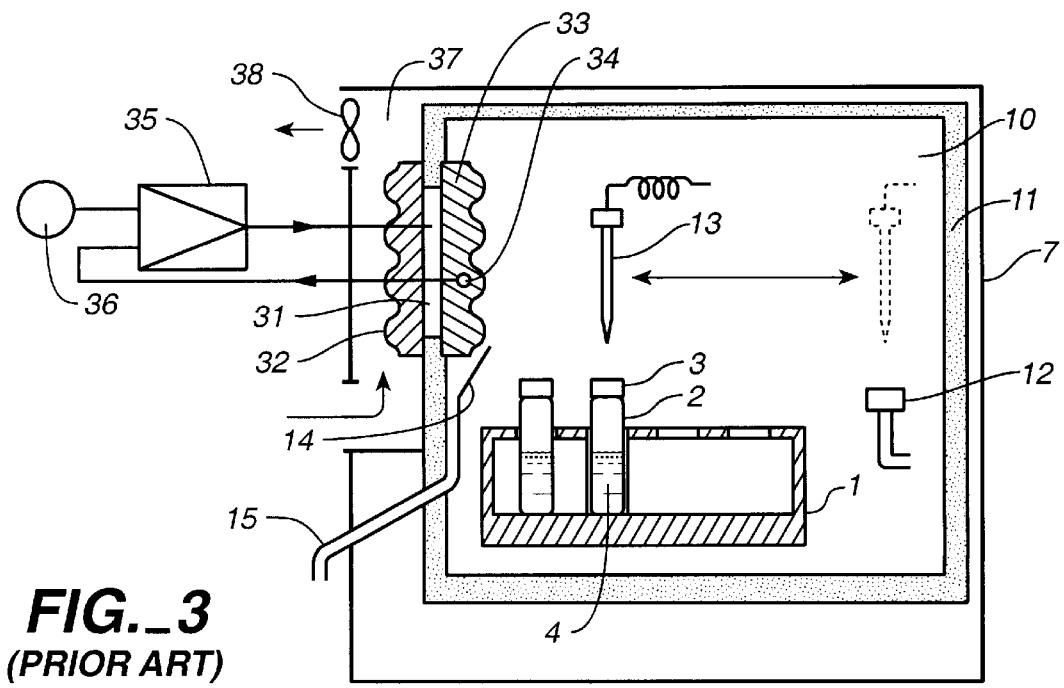
FIG._3
(PRIOR ART)

SAMPLE COOLING APPARATUS AND METHODS

BACKGROUND OF THE INVENTION

This invention relates to sample coolers for cooling liquid samples and keeping them cool before they are subjected to an analysis by an apparatus for automatically analyzing a liquid sample such as a liquid chromatograph. The invention relates also to methods of cooling such liquid samples and keeping them cool.

A liquid chromatograph carries out an automatic analysis by mounting vessels preliminarily sealing in small amounts of samples to a rack, setting this rack to an automatic sample injector, causing the automatic sample injector to sequentially suck up the samples from these vessels mounted to the rack and injecting them into the liquid chromatograph according to a specified program. In most situations, those of the samples on the rack waiting to be analyzed are left under the condition of a room temperature but there are also situations that some of the samples must be kept at a lower temperature condition in order to prevent decomposition or deterioration. In such a situation, a sample cooler is employed in order to keep the sample under a cooled condition.

Conventional sample coolers are either of the direct cooling type or of the air cooling type. A sample cooler of the direct cooling type uses a rack made of a metallic material with high thermal conductivity and a cooler such as a Peltier element is attached to the bottom of the rack such that the temperature of the sample can be controlled mainly by heat conduction through solid materials. With a sample cooler of the air cooling type, essential parts of the automatic sample injector including the rack are enclosed inside a heat insulating case and the air inside the case is cooled such that the sample temperature is controlled through the air.

Next, these two kinds of conventional sample coolers will be explained more in detail.

FIG. 2 shows one of conventional sample coolers of the direct cooling type. The user will initially place liquid samples 4 inside vessels 2 (usually small glass bottles) and closes each of their openings with a septums 3. (Strictly speaking, numeral 3 indicates both a cap and a septum but is herein simply referred to as the "septum".) These vessels 2 are mounted onto a rack 1 taken out of an automatic sample injector 7. The rack 1 is made of aluminum and is provided with about 100 holes 5 for accepting these sample-containing vessels 2. Heat (including cold heat) is transmitted to these vessels 2 through the bottoms, as well as the inner surfaces, of these holes 5.

After the sample-containing vessels 2 are mounted to the rack 1, the rack 1 is set on top of a metallic block 23 inside the injector 7. The metallic block 13 is adapted to be cooled by means of a Peltier element 21 attached to its bottom surface, while its upper surface makes a close contact with the bottom of the rack 1 so as to serve as an efficient heat conductor therebetween. It now goes without saying that the rack 1 itself also serves as an efficient heat conductor to the vessels 2.

Numeral 25 indicates a temperature controlling circuit. Its function is to compare a target temperature set through a target temperature setting means 26 and a signal received from a temperature sensor 24 which is buried inside the metallic block 23 and is adapted to detect its temperature and to control the electric current flowing to the Peltier element 21 such that the difference between the temperature of the metallic block 23 and the target temperature will approach zero and hence that the temperature of the liquid samples 4 will be kept at the level of the target temperature. Attached to the back surface (the heat-radiating surface) of the Peltier element 21 on the side facing the interior of an air duct 27 are heat radiating fins such that the heat transmitted from the metallic block 23 is radiated out and away through these fins and with the aid of an air current caused by a fan 28.

The rack 1, the vessels 2 and the liquid samples 4 therein are thus maintained at a specified low-temperature level. The rack 1 is covered with a heat insulating cover 6 in order to be kept at the desired low-temperature level. The top parts of the vessels 2 surrounding their septums 3, however, are exposed from this cover 6 such that samples can be extracted therethrough by means of a sampling needle 13.

The sampling needle 13 is adapted, according to a program, to move freely not only forward, backward, to the left and to the right but also upward and downward by means of a suitable mechanism (not shown), to draw a liquid sample 4 from a vessel 3 by penetrating its septum 3, to transport the drawn liquid sample 4 to the inlet 12 of the liquid chromatograph and to inject the transported liquid sample 4 into the chromatograph so as to have an analysis carried out. Since each analysis by the liquid chromatograph takes tens of minutes, some of the liquid samples 4 mounted to the rack 1 may have to wait for tens of hours before they are analyzed. Since the liquid samples 4 are maintained at a desired low-temperature level, however, decomposition and deterioration of the liquid samples can thus be avoided.

FIG. 3, in which some of like components are indicated by the same numerals as in FIG. 2, shows one of conventional sample coolers of the air cooling type. An essential portion of the automatic sample injector 7 including the rack 1 having sample-containing vessels 2 set thereon is enclosed inside a heat insulating wall 11 to form a thermostatic chamber 10. Although not shown in FIG. 3, a portion of the heat insulating wall 11 is provided with a door through which the rack 1 can be moved into and out of its interior. Unlike the rack for the direct cooling type, the rack 1 for the air cooling type is made of a porous thin plate of a metallic material in order to allow air to circulate and to reduce its heat capacity since air is the heat-carrying medium in the air cooling type. Thus, the space surrounding the vessels 2 mounted to the rack 1 and the space inside the thermostatic chamber 10 are thermally equivalent.

A Peltier element 31 is again used as a cooling device. Since this cooling device is for cooling the air inside the chamber, the metallic block 33, onto which the heat-absorbing surface of the Peltier element 31 is attached, is provided with fins on its inner surface facing the interior of the thermostatic chamber 10 so as to improve the efficiency of exchanging heat with the air inside.

A temperature controlling circuit 3 5, like the one described above with reference to FIG. 2, serves to compare a target temperature set through a target temperature setting means 36 and a signal received from a temperature sensor 34 which is buried inside the metallic block 33 and is adapted to detect its temperature and to control the electric current flowing to the Peltier element 31, as explained above with reference to FIG. 2. Attached to the heat-radiating surface of the Peltier element 31 on the side facing an air duct 27 are heat radiating fins 32 such that the heat transmitted from the metallic block 33 is radiated out and away through these fins and with the aid of an air current caused by a fan 38.

The cooled air circulates throughout the interior of the thermostatic chamber 10 through natural convection but a fan may be provided inside to cause forced circulation of the air.

Since water vapor in the air is condensed on the surface of the cooled metallic block 33, a draining receptacle 14 and a draining tube 15 connected thereto and leading to the exterior of the thermostatic chamber 10 are provided for discharging the condensed dew. The air inside the thermostatic chamber 10 is thus dehumidified such that the absolute humidity inside is lowered as the temperature drops. The sample-containing vessels 2 on the rack 1 are thus enveloped by cooled and dehumidified air and are maintained at a desired low-temperature level.

Of the two types of sample coolers, the direct cooling type can remove heat with a higher efficiency and the desired low-temperature level can be reached more quickly but the vapor in the atmosphere is condensed during the cooling process. At the time of the sampling, the condensed dew is attached to the tip of the sampling needle 13 and becomes mixed into the sample, tending to adversely affect the accuracy of the analysis. Moreover, the condensed dew may contaminate the vessels 2 and the rack 1 when they are handled.

As for the air cooling type, there is no problem of dew condensation on the vessels 2 or the rack 1 because the cooling is effected with dehumidified air. Since air with a small thermal capacity is used as the thermal medium to cool the entirety of a thermostatic chamber with a large thermal capacity, however, it takes a relatively long time for the cooling. The cooling can be accelerated by using a powerful cooler and providing a fan inside the thermostatic chamber for forced circulation in its interior, but the energy consumption therefor increases faster than the speed of cooling, and hence it is not economically feasible.

SUMMARY OF THE INVENTION

It is therefore an object of this invention in view of the situation as described above to provide an improved sample cooler having the advantages of the both types of cooling described above and having their disadvantaged eliminated.

It is another object of this invention to provide such a sample cooler which is economically operable.

It is additionally an object of this invention to provide a method of cooling liquid samples whereby the advantages of both of the aforementioned types of cooling can be achieved without incurring any significant increase in the expense.

A sample cooler embodying this invention, with which the above and other objects can be accomplished, may be characterized as comprising two cooling mechanisms in addition to a thermostatic chamber in which sample-containing vessels are to be placed. One of the cooling mechanisms ("the first cooling mechanism" serves to cool the air inside the thermostatic chamber, while the other cooling mechanism "the second cooling mechanism") serves to directly cool a heat-conducting block on which the sample-containing vessels are placed and to thereby control the temperature of the liquid samples. A control unit for the cooler controls the operations of these two cooling mechanisms such that the first cooling mechanism is started first but the second cooling mechanism is started with a delay which depends on the occurrence of a certain condition such as when the temperature or humidity inside the thermostatic chamber is detected to have reached a specified level, when condensation of dew is detected inside the thermostatic chamber, or when a predetermined time has elapsed after the operation of the first cooling mechanism was started.

Described more concisely, a rack with a cooling mechanism of a direct cooling type is set inside a thermostatic chamber provided with a cooling mechanism of an air cooling type such that the samples can be cooled directly under a dehumidified condition such that the samples can be cooled quickly without causing dew condensation.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a block diagram of a sample cooler embodying this invention;

FIG. 2 is a block diagram of a conventional sample cooler; and

FIG. 3 is a block diagram of another conventional sample cooler.

Throughout herein, some of like or equivalent components are indicated by the same numerals even where they are components of different devices and may not necessarily be described repetitiously.

DETAILED DESCRIPTION OF THE INVENTION

The invention is described next by way of an example with reference to FIG. 1 in which some of identical or substantially equivalent components are indicated by the same numerals as in FIGS. 2 and/or 3. In FIG. 1, numeral 30 indicates what will be herein referred to as the first temperature control mechanism and includes a Peltier element 31, heat radiating fins 32, a metallic block 33, a temperature sensor 34, a temperature regulating circuit 35, a target temperature setting means 36 and a fan 38. The first temperature control mechanism 30 is of the air cooling type, like the device shown in FIG. 3 and serves to cool the air inside a thermostatic chamber 10 surrounded by a heat insulating wall 11. Numeral 20 indicates what will be herein referred to as the second temperature control mechanism and includes a Peltier element 21, heat radiating fins 22, a metallic block 23, a temperature sensor 24, a temperature regulating circuit 25, a target temperature setting means 26 and a fan 20. The second temperature control mechanism 20 is of the direct cooling type, like the device shown in FIG. 2 and serves to cool sample-containing vessels 2 mounted to a rack 1 made of a thermally conductive material.

The first temperature control mechanism 30 is activated first. As the surface temperature of the metallic block 33 (or that of the fins) drops and the air therearound is cooled and reaches its dew point, condensation takes place on the surface of the fins. The air inside the thermostatic chamber 10 keeps coming into contact with the fins by diffusion and natural convection such that its temperature goes down. At the same time, its water component is removed gradually and its absolute humidity also drops. Since the air has a small thermal capacity, it is cooled to the target temperature within a relatively short time but the temperature of the rack 1 and the vessels 2 thereon lags somewhat behind.

As the temperature of the air inside the chamber 10 approaches the target temperature, the second temperature control mechanism 20 is activated by a control unit 29 in response to a signal from the temperature sensor 16 such that the vessels 2 and the rack 1 begin to be cooled. Since the absolute humidity of the atmosphere is already lowered by this time, the sudden cooling does not give rise to any dew condensation. Since the cooling is by a direct cooling type, the temperature drops quickly to the target low-temperature level. In principle, a same target temperature is set for both temperature control mechanisms 20 and 30 and hence the air inside the chamber 10 and the rack 1 reach eventually the same temperature. Thus, unlike the operation of a conventional cooler of the direct cooling type, it is not necessary to cover the rack 1 with a heat insulating cover although it goes without saying that nothing prohibits the use of such a cover.

The example described above is not intended to limit the scope of the invention. Many modifications and variations are possible within the scope of the invention. Although the example described above is for an application wherein the control unit 29 serves to control on the basis of the temperature information inside the chamber, a humidity sensor (not shown) for detecting the absolute humidity may be used instead of the temperature sensor 16 as a more direct method such that the control unit 29 will begin to function after receiving a signal from such a humidity sensor and thereby ascertaining that the absolute humidity inside the chamber has dropped to a specified level.

In the above variation, since the temperature and the absolute humidity inside the chamber drop after a known period of time has passed since the first temperature control mechanism 30 begins to operate, the control unit 29 may be replaced by a simple timer (not shown) such that the operation of the second temperature control mechanism 20 is started after this known period of time has passed since the first temperature control mechanism 30 began to operate.

As a sensor for detecting humidity, a dew condensation sensor (not shown) may be attached to the surface of the rack 1 or the metallic block 23. According to this variation, the operation of the second temperature control mechanism is stopped when dew condensation is detected by the dew condensation sensor and is restarted when the dehumidification inside the chamber has progressed sufficiently and the dew condensation detector outputs a signal indicative of the disappearance of the condensed dew. This method is advantageous wherein the cooling of the rack 1 can be continued while the dehumidification process is carried out such that the cooling to the target temperature can be accomplished within a shortest time.

It also goes without saying that the application of this invention is not limited to the use with a liquid chromatograph. It should be clear that the present invention is equally well applicable to analyzers of other types for analyzing liquid samples. The invention is applicable to all kinds of devices for carrying out pretreatment of samples, reaction devices and devices for storing samples.

Although the use of a Peltier element was disclosed above, use may also be made of a cooling device of the type which makes use of heat absorption by vaporization at the time of an adiabatic expansion or a method of circulating a cooling liquid cooled outside the system with a pipe system. In other words, many modifications, variations and substitutions are possible. Essential requirements are that the first temperature control mechanism be a mechanism for cooling the space inside the chamber by a cooling means to thereby maintain the space inside at a specified low-temperature level and the second temperature control mechanism be a mechanism for controlling the sample temperature by causing the cooling means to cool the sample-containing vessels through heat-conducting media.

In summary, a rack with a temperature control mechanism of a direct cooling type is contained inside a thermostatic chamber for a cooler of an air cooling type such that the cooling is effected directly and under a dehumidified condition such that the operation of the temperature control mechanism of the direct cooling type is stopped while the interior of the chamber is sufficiently dehumidified. As a result, the cooling can be effected efficiently but without dew condensation. Moreover, the energy consumption does not increase by this invention, compared to the operation of conventional devices.

What is claimed is:

1. A sample cooler comprising:
   a thermostatic chamber containing therein sample-containing vessels;
   a first cooling mechanism for cooling air inside said thermostatic chamber;
   a second cooling mechanism apart from said first cooling mechanism for controlling temperature of said vessels through heat-conducting members; and
   a control unit for controlling operations of said second cooling mechanism based on data on atmospheric condition inside said thermostatic chamber.

2. The sample cooler of claim 1 wherein said data are on temperature inside said thermostatic chamber.

3. The sample cooler of claim 1 wherein said data are on humidity inside said thermostatic chamber.

4. The sample cooler of claim 1 wherein said data are on dew condensation inside said thermostatic chamber.

5. The sample cooler of claim 4 further comprising a dew condensation detector which transmits a signal to said control unit when dew condensation is detected inside said thermostatic chamber.

6. The sample cooler of claim 1 wherein said first cooling mechanism includes means for draining condensed dew.

7. The sample cooler of claim 1 wherein said control unit includes a sensor for detecting atmospheric condition inside said thermostatic chamber.

8. A sample cooler comprising:
   a thermostatic chamber containing therein sample-containing vessels;
   a first cooling mechanism for cooling air inside said thermostatic chamber;
   a second cooling mechanism apart from said first cooling mechanism for controlling temperature of said vessels through heat-conducting members; and
   a control unit for controlling operations of said second cooling mechanism based on time elapsed after operation of said first cooling mechanism is started.

9. The sample cooler of claim 8 wherein said control unit comprises a timer.

10. The sample cooler of claim 8 wherein said first cooling mechanism includes means for draining condensed dew.

11. The sample cooler of claim 8 wherein said control unit includes a sensor for detecting atmospheric condition inside said thermostatic chamber.

12. A method of cooling liquid samples in vessels, said method comprising the steps of:
    placing said vessels on a block made of a heat-conducting material;
    placing said vessels and said block inside a thermostatic chamber;
    operating a first cooling mechanism to cool air inside said thermostatic chamber while monitoring a specified condition; and
    beginning to operate a second cooling mechanism for controlling temperature of said samples by cooling said block when occurrence of said specified condition is detected.

13. The method of claim 12 wherein said specified condition occurs when temperature inside said thermostatic chamber drops to a specified level.

14. The method of claim 12 wherein said specified condition occurs when humidity inside said thermostatic chamber reaches a specified level.

15. The method of claim 12 wherein said specified condition occurs when dew condensation is detected.

16. The method of claim 12 wherein said specified condition occurs when a specified length of time has elapsed after said first cooling mechanism begins to operate.

* * * * *